United States Patent [19]

Natelson

[11] 3,951,605

[45] Apr. 20, 1976

[54] INSTRUMENT FOR AUTOMATED IMMUNOCHEMICAL ANALYSIS

[75] Inventor: Samuel Natelson, Chicago, Ill.

[73] Assignee: Rohe Scientific Corporation, Santa Ana, Calif.

[22] Filed: Aug. 8, 1974

[21] Appl. No.: 495,671

[52] U.S. Cl. .............................. 23/253 R; 23/259; 73/423 A; 141/130
[51] Int. Cl.² .................. G01N 31/20; G01N 1/10; G01N 33/16
[58] Field of Search ................ 23/253 R, 259; 73/423 A; 141/130

[56] References Cited
UNITED STATES PATENTS

| | | | |
|---|---|---|---|
| 3,430,497 | 3/1969 | Tenczar | 73/423 A |
| 3,683,977 | 8/1972 | Crowe et al. | 141/130 |
| 3,684,452 | 8/1972 | Bessman | 23/259 X |
| 3,753,657 | 8/1973 | Downing et al. | 23/253 R |
| 3,764,268 | 10/1973 | Kosowsky et al. | 23/253 R |
| 3,795,149 | 3/1974 | Gillette et al. | 73/423 A |
| 3,802,782 | 4/1974 | Natelson | 23/253 R X |

Primary Examiner—Joseph Scovronek
Assistant Examiner—Barry I. Hollander
Attorney, Agent, or Firm—George B. Oujevolk

[57] ABSTRACT

An instrument for quantitative analysis to measure a minute quantity of antigens or antibodies in a sample. There is a defined travel path for holding sample container holding means thereon, moving means coupled to said travel path to move a plurality of containers in a gang along said travel path, a work station including sensing means to sense a passing container in the container gang to align the containers at said work station. Probes at the work station are disposed above the containers when aligned at the work station. Lift means are provided for lowering and raising the probes into and out of the containers so as to add and remove liquid therefrom and program means control the operation of the instrument including the repetitive addition and removal of fluid from the containers whereby reagents are added to said containers, to lay down a film of immunologically active substance on walls of the containers. Liquid is then removed from the containers and the containers are washed repetitiously by successive additions and removals of a wash solution so as to leave the tubes coated with the immunologically active substance free of contaminating impurities.

5 Claims, 12 Drawing Figures

INSTRUMENT FOR AUTOMATED IMMUNOCHEMICAL ANALYSIS

BACKGROUND OF THE INVENTION

The present invention relates to an instrument for immunochemical analysis, micro-quantitative analysis and more particularly to an instrument useful in antigen/antibody analysis.

THE PROBLEM

An important branch of analysis developed in recent years is immunochemical analysis. In this procedure, a component of some biological fluid, present in minute amounts, is assayed. The materials to be analyzed encompasses a wide range of substances, such as toxic drugs, proteins and polypeptide hormones, polysaccharides and nucleic acid derivatives.

These procedures are tedious and time consuming. A major problem is the large numbers of tests which have to be done even to analyze a single specimen. The reason for this is that in carrying out this procedure, one needs to use serial dilutions in order to explore the range of concentration in which the unknown might be. In effect, standard curves need to be extended and carefully controlled with replicates in order to assure a reasonable degree of accuracy. Hundreds of test tubes are used in the tests.

To understand the instrument, it is first necessary to understand the problem. Let us assume that it is desired to test human blood for morphine content. First, antigenantibodies are produced. This is done by injecting a rabbit with a morphine, coupled to albumen (antigen). The animal then produces antibodies. These antibodies are then used to coat the wall of a test tube. If human blood is then introduced into the test tube, the morphine (antigen) will adsorb to the antibody and thus the wall of the test tube. The problem then is to assay the quantity of morphine. This can be done by using radioactive morphine and adding a predetermined quantity of the radioactive morphine to the blood sample before placing the blood sample in the presence of the test tube containing the antibodies. For example, assume that 100 test tubes are treated so that the walls are coated with antibodies. Then a sample of suspected blood is prepared and mixed with a quantity of radioactive morphine, the quantity of radioactive morphine being so selected as to be of the order of the concentration of morphine in the blood. As is well known, radioactive morphine can be detected by suitable counting equipment measuring the disintegrations. Then the blood sample with the added radioactive morphine is serially diluted and some added to each of a series of test tubes containing the antibody. The test tubes are then emptied and washed out with a dilute saline solution. The morphine antigens in the sample, namely both those of the blood sample, as well as the added radioactive antigens will adhere to the walls. However, since the quantity of morphine antigen is larger than the quantity of antibodies, only a portion of the morphine will adhere to the wall. Some of the morphine adhering to the wall will be radioactive morphine and some unknown sample morphine. The more radioactive morphine adheres to the wall, the less morphine is in the sample, and the less radioactive morphine adhering to the wall, the more morphine there is in the sample. With only one test tube, no significant information is obtained, but with test tubes having many dilutions, a range can be found where the balance between antigens adsorbed and not adsorbed is a function of the concentration of morphine in the blood. This range needs to be found by trial and error and therefore the need for serial dilutions and for many test tubes. In addition, many standards need to be run to set up a standard curve.

By repeating the foregoing with a different quantity of radioactive morphine, e.g., one-half the previous quantity, significant results can be obtained. Since the quantity of radioactive morphine is known, proper equations can be set up to solve for the unknown quantity of morphine in the sample. However, as is readily apparent, this procedure requires large numbers of test tubes which must be hand filled and handled, making it a long and tedious process and subject to human error.

OBJECTS OF THE INVENTION

The object of this invention is to fabricate an instrument which can process large numbers of test tubes rapidly. This includes rinsing the tubes to remove unwanted impurities without removing solid adsorbant in the tube, either as granules or other solid form. All of this needs to be done rapidly, without requiring the attention of the operator. By rapidly, is meant a rate exceeding the adding of a reagent to at least 100 tubes per minute.

The invention, as well as other objects and advantages thereof, will become more apparent from the following detailed description when taken together with the accompanying drawings, in which:

DETAILED DESCRIPTION

Figure 1:
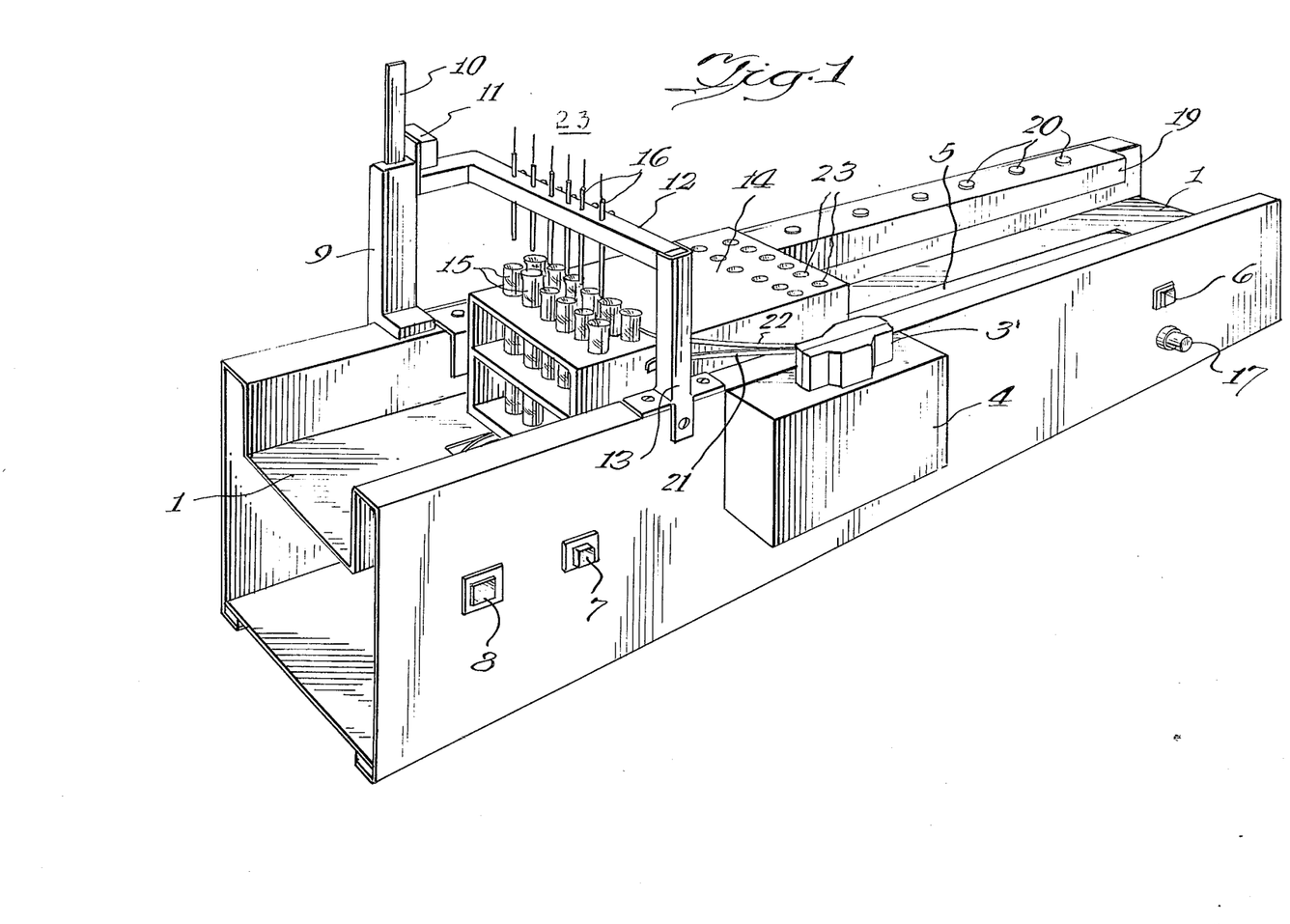
FIG. 1 is a longitudinal perspective view of the instrument.
Figures 2, 3:
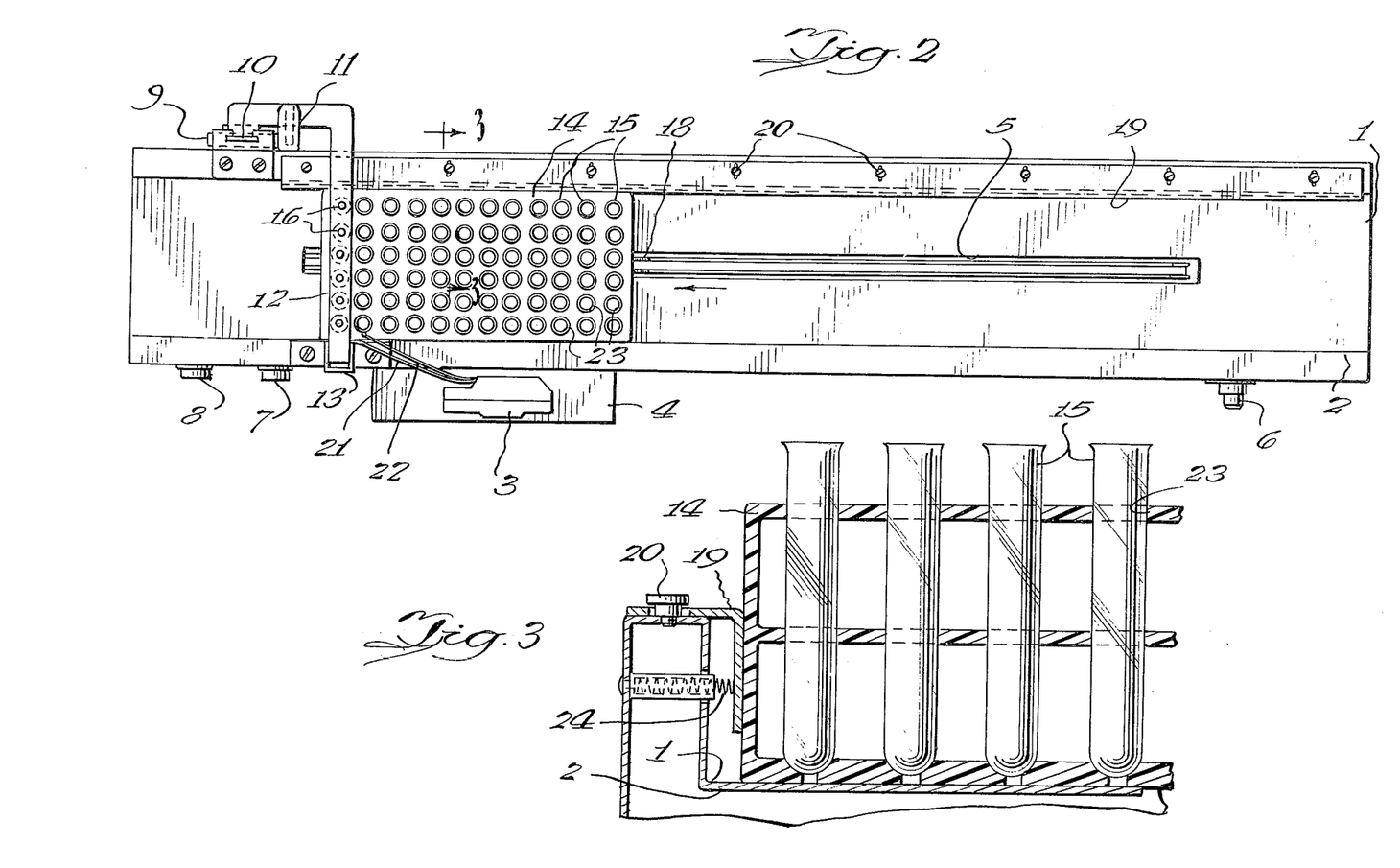
FIG. 2 is a top view of the instrument shown in FIG. 1.
FIG. 3 is a part of a sectional view along line 3 of FIG. 2.

The instrument herein contemplated which will carry out the invention is shown in FIGS. 1 and 2. In this figure is shown a slotted track 1 on which rests a rack 2 with holes 3 for supporting test tubes 15. This rack is pushed along the slotted track, made of polished stainless steel, by a chain drive 5 which has a projection 18 attached to it so that as the chain moves in a horizontal plane, it pushes the rack ahead. This type of drive has already been shown in U.S. Pat. No. 3,802,782 (FIGS. 1A and 1B).

As an alternative, the rack is fabricated of styrene plastic, as an example, and depressions pressed in the plastic so that the form simulates a rack with test tubes. In this way, a disposable rack and container is utilized.

A double switch 3', with two independent arms 21 and 22, intercepts the rack. Arm 21 senses the rack itself, and arm 22 senses the test tubes which are in the rack.

A latching relay is housed in a housing 4. The purpose of this latching relay is to insure the sensing of the rack from tube to tube without intermediate stoppage. The objective is for the rack to move in order to present a row of test tubes 15 to probes 16. After completion of the operation, for which the instrument is programmed, the rack needs to move to the next row of test tubes automatically. Arm 22 coupled with switch 3' and relay housing 4 assures this motion.

Figure 4:
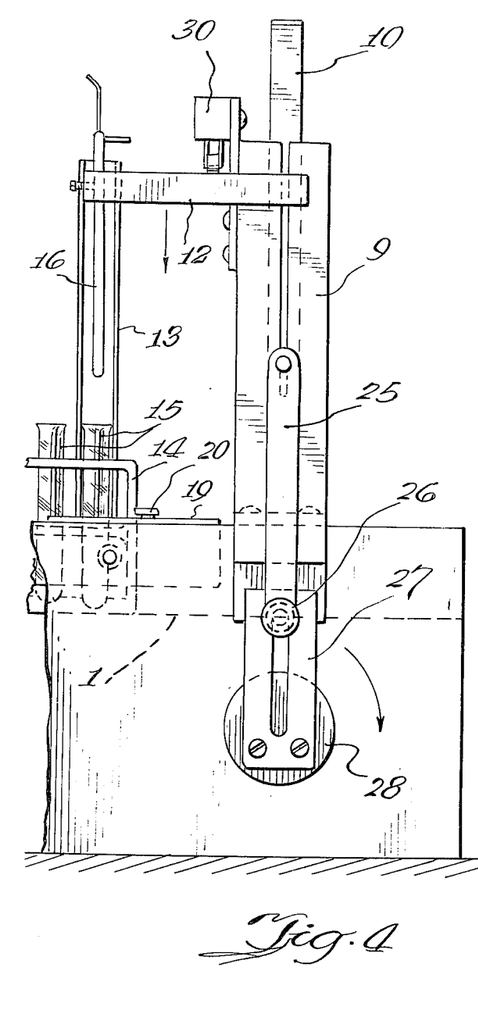
FIG. 4 shows a side view of a portion of the instrument opposite the side shown in FIG. 1.
Figure 5:
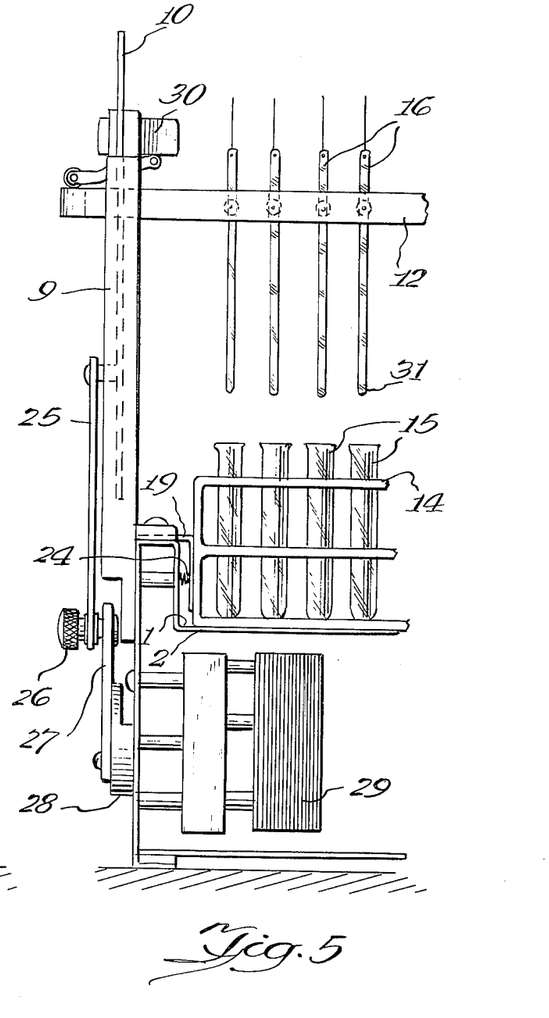
FIG. 5 presents a sectional view corresponding to the side view shown in FIG. 4.

The probes 16 are supported on arm 12 which rides up and down in guide arm 13. Arm 12 is pinned and supported on slide 10 which can move up and down in guideway 9. Slide 10 is moved up and down by first connector 25 and second connector 27 (FIGS. 4 and 5). The second connector is pinned off center to wheel 28, so that as the wheel rotates, the second connector pulls adjustable pivot 26 so as to pull arm 25, which is pivoted on slide 10. This can be seen best in FIG. 4.

From FIG. 4 one can see that the extent of travel of slide 10 up or down is controlled by the position of pivot 26 in slot on 27. As this pivot is moved down the extent of travel is shortened.

From FIG. 4 it can also be seen that when slide 10 moves down, arm 12 moves down and thus probe 16 moves down into the test tubes. Arm 12 moves also in guide 13 so that it moves directly up and down and does not sway.

Switch and light combination 6 switches on the power. The fuse is shown at 17. The switch and light combination 7 is a bypass to move the arm 12 down or up at will so as to set the instrument in phase or for testing purposes.

Switch 8 sets the mode to be operated in. This will be described later.

In order for the system to accomodate racks of somewhat different widths, one side wall 19 of the rack is spring loaded and adjustable in position by means of guides 20 which rest in a slot and can be tightened at a particular position. Between rack wall 19 and the instrument wall are springs 24 (FIG. 3) which keep wall 19 snug to the rack. This arrangement can be seen in top view FIG. 2 and sectional view FIG. 3. The test tubes 15 aligned under the probes 16 defines a work position 23.

The mechanism for raising and lowering the arm 12 is best seen in FIG. 4 and FIG. 5. A safety switch 30 is provided, so that the signal is available to tell when the probes are in the vertical position. This switch is in series with the drive motor which pushes the chain and rack (not shown) and thus the rack cannot move forward while the probes are in the down position. The probes are raised or lowered by lift motor 29. The adjustable pivot 26 permits the adjustment of the extent of lift as described above.

The detail of the structure of the particular set of probes is shown in FIGS. 6, 7, 8 and 9. These probes are used to add a solution to the test tube or remove it without removing any suspended particles. In effect, they act as a system for washing a precipitate held in the test tube. The entrance of wash fluid is at tube 32, the exit is through tube 33. The lower part of the probe 31 is porous. This can be porous ceramic, porous plastic or porous stainless steel or made of sintered glass. The solution to be used enters at 32 and is aspirated at 33. This process can be repeated as often as required. Tube 34 is for the addition of any additional reagent as desired.

Figures 10, 11:
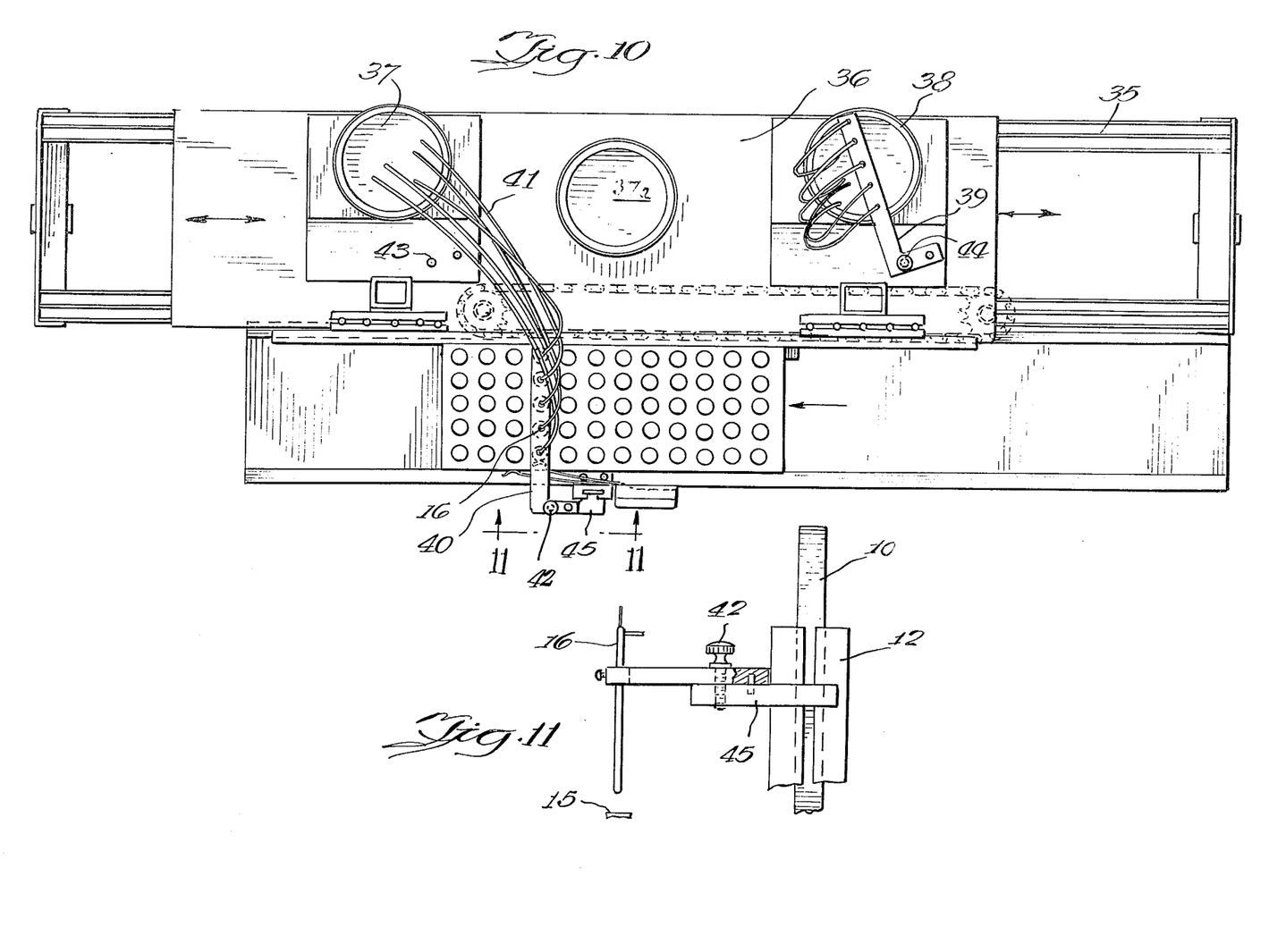
FIG. 10 shows a top view of a work station in the instrument contemplated herein.
FIG. 11 is a view along lines II — II of FIG. 10.

FIG. 10 is a top view of the instrument assembled with the dispensers which add the solution to the test tube. The dispensers used are multiple dispensers described in U.S. patent application Ser. No. 297,797, now U.S. Pat. No. 3,837,534. They are mounted on shelf support 36 which is fitted with bearings which slide in a track 35. Thus, as one pushes the shelf support back or forth it permits the bringing of every one of the three dispensers to the work station located at 23. By loosening and removing knurled nut 42, the manifold 40 holding the probes 16 can be lifted off and placed on support 43.

In FIG. 10, dispenser 37 is in position for delivering the solution and dispenser 38 is in rest position with its manifold 39 on vertical threaded rod 44. Thus, manifold 39 or 40 can be used without resorting to long tubing since the dispenser is brought close to the dispensing station. An additional dispenser 37a is indicated on the shelf support. Normally, four such dispensers are available, allowing flexibility to the instrument. In FIG. 10, the chain drive is shown in a horizontal plane and the rack is pushed from one side. In FIG. 1 the chain drive is in a vertical plane and the rack is pushed at the bottom.

The detail in FIG. 11 shows how the knurled screw 42 is removed to permit exchange of manifolds. The screw 42 threads into support 45 on slide 10.

Figure 12:
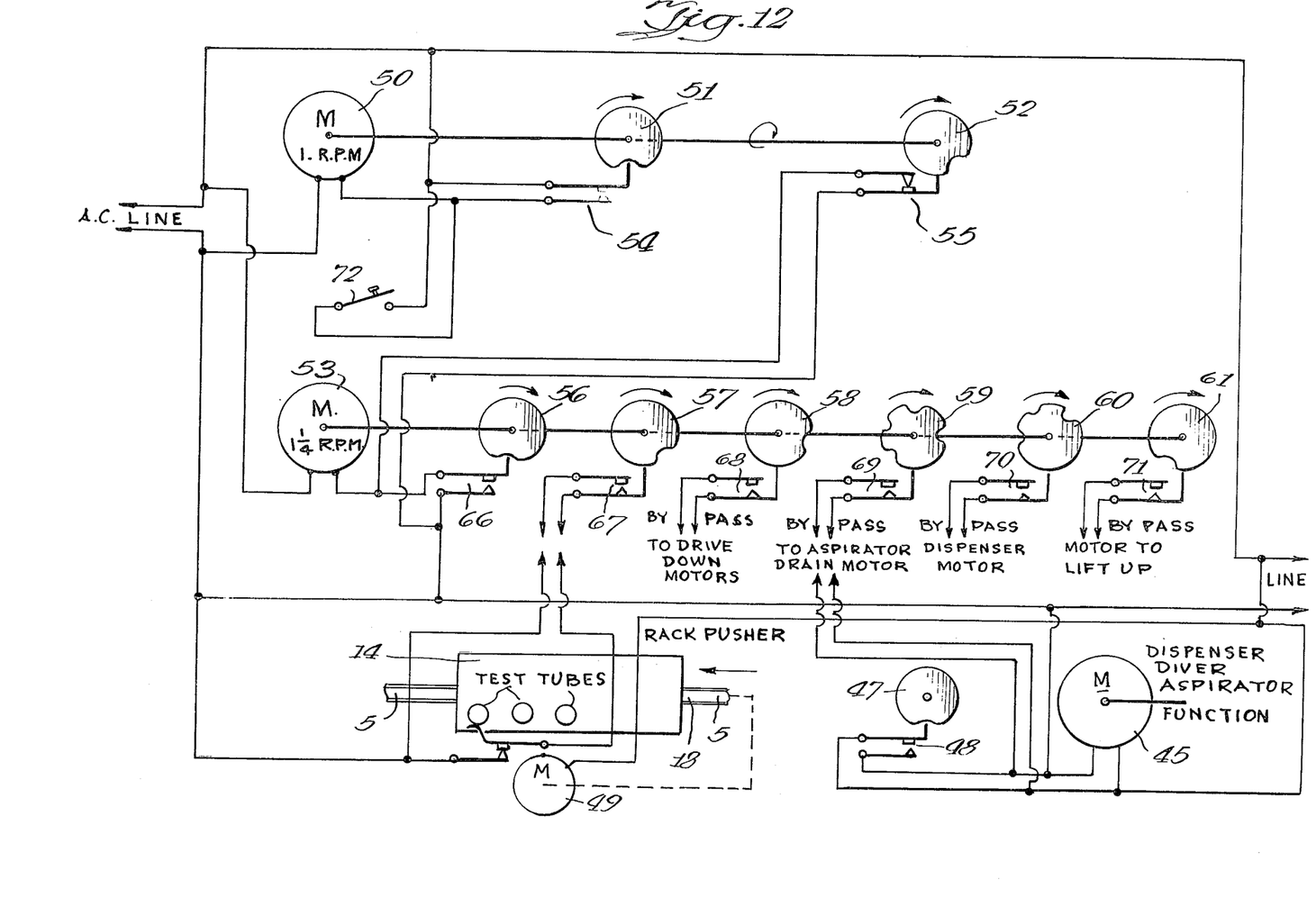
FIG. 12 schematically illustrates the cam action which is used to control the various components herein described.

The control mechanisms for the instrument are shown in FIG. 12. There are two sets of controls; the master control which comprises the 1 rpm motor 50 and cams 51 and 52 and the 1¼ rpm motor with cams 56, 57, 58, 59, 60 and 61.

Switch 54 is in series with motor 50. This switch is normally open. Thus, in the position shown, the motor 50 cannot run. When switch 72 is pressed momentarily, a bypass is provided to motor 50 and it moves. Switch 54 is closed as 51 rotates to press it and will remain closed until it completes a circuit and falls into a depression in the cam. During this circuit it will activate switch 55 which is normally closed, that is, it closes when it falls into the depression. This will provide a bypass to the switch 66 which is in series with the power supply to motor 53 (1¼rpm). This will start motor 53 and permit it to complete a circuit and then stop as switch 66 is inactivated by dropping into depression of cam 56. In summary, when switch 72 is depressed, motor 50 will begin and complete one rotation. During its travel, it will short switch 66 and activate motor 53 so that motor 53 will complete its circuit. Motor 53 will then wait for a second signal to complete a second circuit. Switch 72 will get its signal from switch 3 and relay enclosed in housing 4 indicating that a new set of test tubes has come into place. Motor 50 will not start until it gets the signal from the test tube switch 3.

During a single rotation of motor 53, various functions are carried out. In each case, a bypass is given to a motor of a particular instrument. That instrument then performs its function cycling once and then stopping. Labelling of the motors, dispenser, diver or aspirator function in FIG. 12 indicates that each of these acts in a similar manner. For the motor of the dispenser, the power line goes through a switch 48 in a cam 47. As can be seen from FIG. 12, this switch 48 is resting in the depression of the cam 47 which is operated by motor 45'. The power cannot reach the motor and therefore the motor cannot operate. When cam 59 rotates so that switch 69 falls into the cam depression, switch 69 is closed and supplies a bypass to switch 48. Motor 45 starts. As it runs, arm of switch 48 lifts on the cam 47, the switch staying closed until it completes its cycle and drops into the depression. During this rotation, the dispenser pumps the fluid to be delivered.

Using this general principle, we can now examine motor 53 and its action as it completes a cycle. Receiving a bypass from switch 55 it starts to rotate. From cam 57, and switch 67, it signals the drive motor (not shown) to advance the test tube rack to the next row of empty tubes. Cam 58 and switch 68 now signal the dive down motor 29 (FIG. 5) to lower the probes into the test tubes. Cam 59 and 60 have multiple depressions to aspirate the solution in the test tube, add solution, aspirate, add solution, aspirate, etc., as many times as desired. In the figure, four aspiration and three dispense signals are given, the aspiration being the last act. In this way, the tubes are rinsed and emptied. Finally, cam 61 and switch 71 signal to lift up the motors. The rotation is stopped until a second signal is given by closure of switch 72 to start the cycle again. If switch 72 is placed in a locked position, the system will cycle repetitively and indefinitely until the last tubes in the rack are completely washed. Since motor 53 completes its cycle before motor 50, the timing is such that no interference of the cycles occurs.

Switch 8 is a spring return switch which is used to start the cycle by shorting switch 72. If switch 8 is kept in a locked position, cycles will continue indefinitely. Cam 28 of FIG. 5 has two depressions (180° apart, not shown), so that a switch placed in a particular position will stop the motor 29 twice. By placing the switch in a suitable position, a momentary bypass will cause the motor to move 180° causing the probes to be lowered. A second momentary bypass will cause it to move a second 180° and thus lift up. This switch is bypassed by switch 68 of cam 58 in FIG. 12 on the down stroke and cam 61 and switch 71 on the upstroke. If the instrument is to be used as a tube filler only, then switches 68, 69 and 71 are disconnected. Cam 60 and switch 70 can be used to add the solution but it is better to disconnect this cam and add an additional cam with a single depression so that a single cycle will cause the dispenser to dispense only once.

The operation of the instrument is best seen from typical examples of its use.

EXAMPLE I

In testing for albumin in minute quantities in urine or blood, using nanoliter volumes of biological fluid as obtained, by micropuncture from the kidney or bloodstream of a mouse, one first injects purified albumin from the mouse into a rabbit to generate antibodies to the albumin. One then isolates by conventional procedures the antibody to the albumin from the rabbit. Mouse albumin is then iodinated with radioactive iodine by conventional means. The reagents to be used then are radioactive albumin, ordinary albumin and the antibody to albumin.

To carry out the test, the rack is filled with test tubes. These test tubes have walls made of adsorbent material such as glass or styrene resin. Dispenser 37 is set up with a dilute solution of antibody. One ml of solution is dispensed into the tubes of the first row. The drive motor is inactivated in this case. The rack advances, the solution is squirted into the tube and the rack advances. The solution is squirted into the second row of tubes. The total elapsed time is 3 seconds per row or six tubes in 3 seconds or 120 tubes per minute. Note that switch arm 21 senses when the rack is in position and arm 22 senses the tubes. The operation continues until all the tubes have been processed.

The objective here is to coat the tubes with antibody. After the solution has been added to the tubes, the rack is removed and allowed to stand for several hours or overnight. The rack is now returned to the instrument, manifold 40 is removed and the shelf support slid over and manifold 39 is attached returning manifold 40 to its resting position at post 43. Dispenser 38 is now in place. The drive motor is now activated. The aspirator of U.S. patent application Ser. No. 297,797 is attached to end tube 33 of the probes of FIGS. 6, 7, 8 and 9 which are ganged together.

The rack advances to the first row, the probes dive down into the test tubes. The aspirator is activated by cam 69 and the antibody solution is aspirated. Cam 60 activates the dispenser which squirts in 3 ml of normal saline (wash solution). The aspirator removes this. Again 3 ml is squirted in and then removed. This is repeated again. Finally, the solution is aspirated, leaving the tube rinsed. The object is to remove excess antibody and leave only that adsorbed to the wall of the test tube which is made of adsorbent material such as glass or styrene resin as hereinbefore described.

Figures 6, 7, 8, 9:
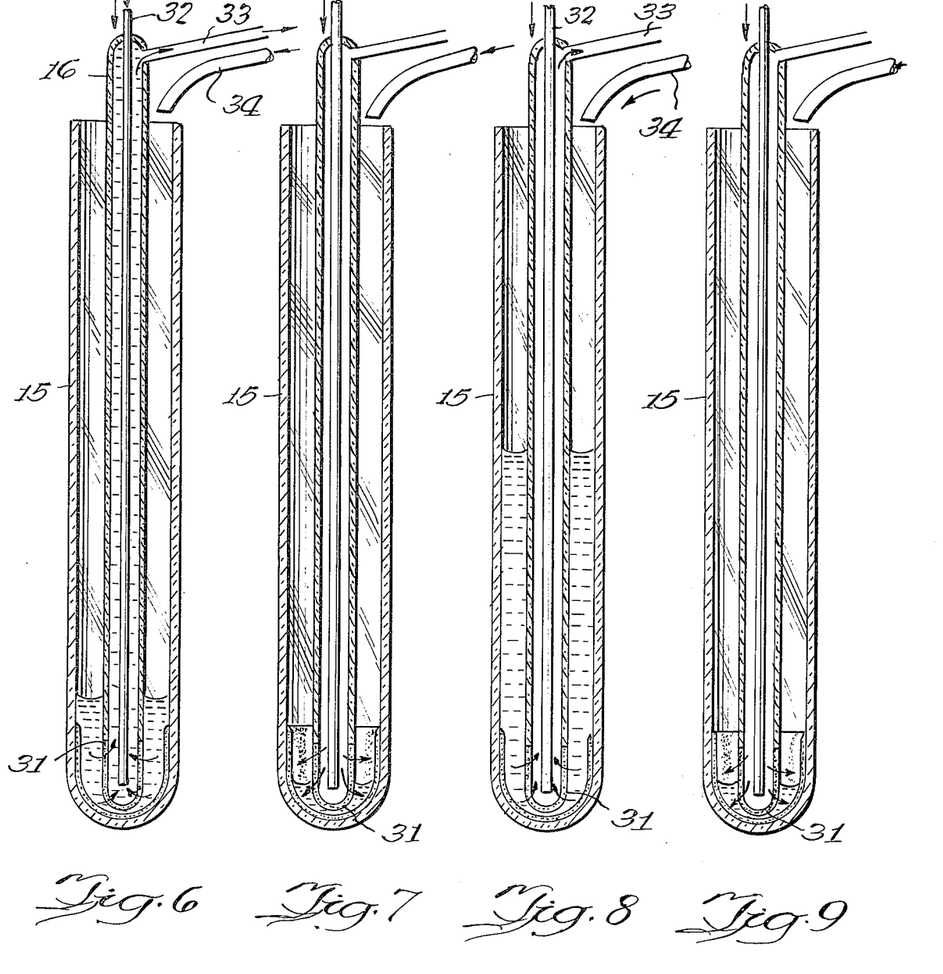
FIGS. 6, 7, 8 and 9 are each a sectional view of a test tube depicting the action taking place therein.

FIGS. 6 to 9 show this sequence. In FIG. 6, the coated wall is shown. The original antibody solution (1 ml) is being aspirated. In FIG. 7, saline is being added (3 ml). In FIG. 8 the 3 ml is being aspirated again and in FIG. 9 wash solution is being added again.

As can be seen from FIG. 12, a row (six tubes) is being washed every minute. A rack of 60 tubes will thus be washed each with four washes in a period of 10 minutes.

The coated tubes may be stored indefinitely in the refrigerator if they are not allowed to dry out.

To assay an unknown sample for albumin, the rack is returned to the instrument and a dilute solution of radioactive albumin is squirted into each tube from a dispenser as described above, the operator now adds a minute amount of test material such as urine or blood to each tube either manually or by a transfer instrument as shown in U.S. Pat. No. 3,687,632 and allows the solution to equilibrate. The instrument of FIG. 1 is set in the wash out mode and excess radioactive iodinated albumin and the sample is washed out. The tubes are now transferred to a radioactive counting chamber and the residual radioactivity is measured.

What has taken place is that the albumin in the sample and the radioactive albumin both compete for binding sites on the adsorbed antibody. After washing out the excess, the amount of radioactive albumin on the wall is inversely proportional to the amount present in the original serum. Thus, the more radioactivity left on the test tube walls, the lower the concentration of sample albumin. Results can be evaluated by comparison with a standard curve. The albumin in a few nanoliters of biological fluid can be determined in this manner.

EXAMPLE II

Since albumin can be combined with many compounds such as morphine or steroids by chemical means, an animal is now immunized against this combination and the antibody is obtained from the animal.

The tubes are coated with this antibody and these can be used for the determination of the particular substance bound to the albumin, such as morphine and cortisone in the same manner as described for albumin.

EXAMPLE III

A solid support other than the test tube is used, i.e., activated charcoal, a plastic sponge made from styrene resin, or a solid granular material such as silica is added to the test tube. During the wash cycle, the unwanted solutions filter through the porous area (31) of FIGS. 6 to 9 leaving the solid behind. As the probe lifts, wash solution is added through the porous area to rinse the solid phase down into the test tube. When the test tube is transferred to the counting chamber it contains solvent, but all excess radioactivity is washed out. Thus, the system permits the repeated washing of a precipitate automatically, without removing the precipitate from the test tubes. This permits wide flexibility in choice of an adsorbant.

EXAMPLE IV

It is also practicable to combine an enzyme or a color reagent to a protein such as albumin. Compounds which fluoresce and are bound to albumin can also be assayed. Albumin bound to an enzyme such as alkaline phosphatase may be substituted for radioactive iodinated albumin. A reagent is then added to produce a color with the enzyme. Dinitrophenylphosphate as an example, is hydrolyzed by phosphatase to produce a yellowish orange color. As an alternative, fluorescein tied to albumin may be used. The fluorescence of the adsorbed material may then be measured. In these cases, the test tubes may continue on to a readout zone as in U.S. Pat. No. 3,687,632 and the fluorescence be read directly, and with the aid of a computer be presented in the form of concentration of the unknown.

EXAMPLE V

In place of the antibody to albumin, the antigen (albumin) is coated on the tube as in Example I. In this case, the unknown serum is added with saline and the tube is coated. The saline and impurities are washed off. Antibody solution which has been reacted with radioactive iodine is now added and excess is again washed off. The radioactive material left in the tubes is counted and the amount of antibody found is a measure of the antigen adsorbed to the tube.

As can be seen from the examples above, the instrument provides, in an immunochemical system of analysis:

1. A rapid method for loading test tubes with reagents and coating them automatically with a reagent.
2. A rapid means for rinsing the test tubes of excess reagent added.
3. A rapid means of adding and washing out a color, fluorescent or radioactive reagent which reacts with the coated surface and competes with the substance being tested in a biological fluid.
4. A convenient and automatic means for adding reagent and washing out excess, to a powdered insoluble material contained in a test tube without removing the powdered material from the test tubes.
5. A means for rapidly switching from one reagent to another so that one single instrument can add more than one variety of reagent to the test tubes.
6. And finally presenting a tube containing a signal, such as radioactivity, color or fluorescence which can be read by a readout system so as to determine the concentration of minute amounts of a substance from a biological medium.

I claim:

1. An instrument for quantitative analysis to measure a minute quantity of antigens or antibodies in a sample comprising in combination:
   a. a defined horizontal travel path for receiving holding means thereon; said holding means holding test tubes vertically thereon;
   b. moving means disposed for moving said holding means, coupled to said travel path to move a plurality of containers in a gang horizontally along said travel path;
   c. a work station including sensing means to sense a passing container in the container gang to align the containers at said work station;
   d. probes at said work station disposed above said containers when aligned at the work station;
   e. lift means for lowering and raising the probes into and out of the containers to add and remove liquid therefrom;
   f. program means to control the operation of the instrument including means for the repetitive addition and removal of liquid wash solution from the containers; whereby after reagents are added to said containers to lay down a film of immunologically active substance on the walls of said containers, excess reagent is removed and liquid wash solution is added and removed from said containers thus said containers being washed repetitively by successive addition and removal of wash solution so as to leave the tubes coated with the immunologically active substance free of contaminating impurities, where the immunologically active substance is one of the group defined by antigen and antibody.

2. An instrument as claimed in claim 1 wherein said probes are at least partly porous so that a granular substance to which has been added an antigen or antibody may be rinsed repetitively of impurities.

3. An instrument as claimed in claim 2 including at least two sets of probes, at least two dispensing means for supplying said probes, a manifold for attaching the probes into position, and changing means including a shelf support fitted with slide bearings whereby it is possible to change from one set of probes and its dispensing means to the other set of probes and its dispensing means.

4. An instrument as claimed in claim 1, said travel path having at least one longitudinal spring loaded side wall, which is laterally adjustable to accommodate racks of different widths.

5. An instrument as claimed in claim 4, said lift means comprising an adjustable slide having a vertical guide, and an arm pinned in said guide, connecter crank means connected to said slide, and an off-center wheel connected to said connector crank means whereby as said wheel rotates, said connector crank means raises and lowers said slide.

* * * * *